United States Patent [19]

Hudlicky

[11] Patent Number: 5,488,167
[45] Date of Patent: Jan. 30, 1996

[54] SYNTHESIS OF SPHINGOSINES

[75] Inventor: Tomas Hudlicky, Blacksburg, Va.

[73] Assignee: Virginia Tech Intellectual Properties, Inc., Blacksburg, Va.

[21] Appl. No.: 389,622

[22] Filed: Feb. 21, 1995

Related U.S. Application Data

[63] Continuation of Ser. No. 137,346, Oct. 18, 1993, abandoned.
[51] Int. Cl.$^6$ .................................................. C07C 209/42
[52] U.S. Cl. .................... 564/489; 549/433; 549/434; 549/435; 549/437; 549/476; 552/10; 560/196; 564/507
[58] Field of Search ..................................... 564/489, 507; 549/433, 434, 435, 437, 476; 552/10; 560/196

[56] References Cited

U.S. PATENT DOCUMENTS

| | | | |
|---|---|---|---|
| 4,937,328 | 6/1990 | Schmidt et al. | 536/18.6 |
| 5,012,000 | 4/1991 | Illig et al. | 546/489 |
| 5,068,345 | 11/1991 | Illig et al. | 548/230 |
| 5,110,987 | 5/1992 | Liotta et al. | 564/303 |
| 5,137,919 | 8/1992 | Igarashi et al. | 514/642 |
| 5,151,360 | 9/1992 | Handa et al. | 435/240.2 |
| 5,200,516 | 4/1993 | Hudlicky | 536/41 |
| 5,220,043 | 6/1993 | Dong et al. | 554/82 |

FOREIGN PATENT DOCUMENTS

| | | | |
|---|---|---|---|
| 0204344 | 12/1986 | European Pat. Off. | C07H 3/04 |
| 0300960 | 1/1989 | European Pat. Off. | A61K 31/70 |
| 1-093562 | 4/1989 | Japan | 552/10 |
| 89/12632 | 12/1989 | WIPO | C07D 263/06 |

OTHER PUBLICATIONS

Newman, H., "A Steroselective Synthesis of D–*erythro*–Sphingosine", *Journal of the American Society*, vol. 95., No. 12, pp. 4098–4099 (Jun. 1973).

Raymond Boutin and Henry Rapoport, "α–Amino Acid Derivatives as Chiral Educts for Asymmetric Products. Synthesis of Sphingosine from α'–Amino–α, β–ynones", *Journal of Organic Chemistry*, vol. 51, pp. 5320–5327 (Oct. 1986).

Robin Polt, Matt A. Peterson and Lynn DeYoung, "Aluminoxy Acetals from α–Amino Esters: Chirality Transfer via Sequential Addition of Hydride and C–Nucleophiles, 2–Amino Alcohols and Sphingosines", *Journal of Organic Chemistry*, vol. 57, No. 20, pp. 5469–5480 (Dec. 1992).

Peter Herold, "Synthesis of D–*erythro* and D–*threo*–Sphingosine Derivatives from L–Serine", *Helvetica Chimica Acta*, vol. 71, pp. 354–361 (Sep. 1988).

Sanjay Nimkar et al., "A Steroselective Synthesis of Sphingosine, A Protein Kinase C Inhibitor", *Tetrahedron Letters*, vol. 29, No. 25, pp. 3037–3040 (Sep. 1988).

Mark A. Findeis and George M. Whitesides, "Fumarase–Catalyzed Synthesis of L–*threo*–Chloromalic Acid and Its Conversion to 2–Deoxy–D–ribose and D–*erythro*–Sphingosine", *Journal of Organic Chemistry*, vol. 52, 2838–2848 (Jul. 1987).

Peter Zimmermann and Richard R. Schmidt, "Syntheses von *erythro*–Spingosinen über die Azidoderivate", *Liebigs Annalyitical Chemistry*, pp. 663–667 (Sep. 1988).

Michio Obayashi and Manfred Schlosser, "An Efficient Synthesis of (2S, 3R)– And (2S, 3S)–Sphingosine", *Chemistry Letters*, pp. 1715–1718 (May 1985).

D. T. Gibson, M. Hensley, H. Yoshioka, and T. J. Mabry, "Formation of (+)–cis–2, 3–Dihydoxy–1–methylcyclohexa–4,6–diene from Toluene by *Pseudomonas putida*", *Biochemistry*, pp. 1626–1630 (Jan. 1970).

Tomas Hudlicky et al., "Biocatalysis as the Strategy of Choice in the Exhaustive Enantiomerically Controlled Synthesis of Conduritols", *Journal of Chem. Soc. Perkin Trans. 1*, pp. 2907–2917 (Mar. 1991).

Tomas Hudlicky, Jacques Rouden and Hector Luna, "Rational Design of Aza Sugars via Biocatalysis: Mannojirimycin and Other Glycosidase Inhibitors", *Journal of Organic Chemistry*, vol. 58, No. 5, pp. 985–987 (Nov. 1993).

Tomas Hudlicky, Hector Luna, John D. Price and Fan Rulin, "Microbiol Oxidation of Choloroaromatics in the Enantiodivergent Synthesis of Pyrrolizidine Alkaloids: Trihydoxyheliotridanes", *Journal of Organic Chemistry*, vol. 55, pp. 4683–4687 (Aug. 1990).

Tomas Hudlicky, Hector Luna, Gracieia Barbieri and Lawrence D. Kwart, "Enantioselective Synthesis through Microbial Oxidation of Arenes. 1. Efficient Preparation of Terpene and Prostanoid Synthons", *Journal of American Chemical Society*, vol. 110, pp. 4735–4741 (Feb. 1988).

C. A. Grob and F. Gadient, "Die Synthesis des Sphingosins und seiner Steroisomeren", *Helvetica Chimica Acta*, vol. XL, No. 130, pp. 1145–1150 (May 1957).

Gerben J. Zylstra and David T. Gibson, "Toluene Degradation by *Pseudomonas putida* F1", *The Journal of Biological Chemistry*, vol. 264, No. 25, pp. 14940–14946 (Mar. 1989).

Elmer J. Reist and Pamela H. Christie, "Synthesis of *trans*–and *cis*–Sphingosine", *Journal of Organic Chemistry*, vol. 35, No. 12, pp. 4127–4130 (Jan. 1970).

Peter Somfai and Roger Olsson, "An Enantiospecific Synthesis of D–*erythro*–Sphingosine from D–Tartaric Acid", *Tetrahedron*, vol. 49, No. 30, pp. 6645–6650 (May 1993).

Hirotaka Shibuya, Keiko Kawashima, Masahiko Ikeda and Isao Kitagawa, "Synthesis of Two Pairs of Enantiomeric $C_{18}$–Sphingosines", *Tetrahedron Letters*, vol. 30, No. 51, pp. 7205–7208 (Jun. 1989).

Bruno Bernet and Andrea Vasella, "Enantioselective Synthesis of D–*erythro*–Sphingosine", *Tetrahedron Letters*, vol. 24, No. 49, pp. 5491–5494 (Jul. 1993).

(List continued on next page.)

*Primary Examiner*—Glennon H. Hollrah
*Assistant Examiner*—Scott C. Rand
*Attorney, Agent, or Firm*—Burns, Doane,. Swecker, & Mathis

[57] ABSTRACT

Provided by the present invention is a process for the biocatalytic synthesis of optically pure sphingosines from achiral starting material. The stereoisomers of sphingosine are prepared from chiral arene diols using stereospecific reaction techniques to obtain the desired sphingosine or derivative thereof.

14 Claims, 4 Drawing Sheets

OTHER PUBLICATIONS

Kenji Mori and Yuji Funaki, "Synthesis of (4E,8E,2S,3R,2'R)-N-2'-Hydroxyhexadecanoyl-1-o-β-D-Glucopyranosyl-9-methyl-4,8-Sphingadienine, the Fruiting-Inducing Cerebroside in a Basidiomycete *Schizophyllum Commune*", *Tetrahedron*, vol. 41, No. 12, pp. 2379–2386 (Jan. 1985).

Peter Tkaczuk and Edward R. Thorton, "Useful Synthesis of *erythro*-and *threo*-N-Oleoyl-D-Sphingosines (Ceramides) and Galactosylceramides (Cerebrosides) from L-Serine", *Journal of Organic Chemistry*, vol. 46, pp. 4393–4398 (Feb. 1981).

Philip Garner, Jun Min Park and Elise Malecki, "A Stereodivergent Synthesis of D-*erythro*-Sphingosine and D-*threo*-Sphingosine from L-Serine", *Journal of Organic Chemistry*, vol. 53, pp. 4395–4398 ( May 1988).

Julian N. Kanfer and Sen–itiroh Hakomori, "Sphingolipid Biochemistry", *Handbook of Lipid Research*, pp. 1–9 (1983).

Alfred H. Merrill, Jr. et al, "Structural Requirements for Long–Chain (Sphingoid)Base Inhibition of Protein Kinase C in Vitro and for the Cellular Effects of These Compounds", *Biochemistry, vol. 28, pp. 3138–3145 (Feb. 1989)*.

Herbert E. Carter et al, "Biochemistry of the Sphigolipides", *Journal of Biological Chemistry*, vol. 170, pp. 269–283 (Sep. 1947).

Janet M. Harouse et al, "Inhibition of Entry of HIV–1 in Neural Cell Lines by Antibodies Against Galactosyl Ceramide", *Science*, vol. 253, pp. 320–323 (1991).

Alessandro Bongini et al, "Iodocyclofunctionalization of (Z)-1-Trichloroacetimidoyloxyalk-2-enes and 3-Trichloroacetimidoyloxyalk-1-enes, synthesis of (±)-*erythro*-Sphinganine Triacetate and (±)-*threo-Sphinganine Triacetate*", *Journal of Chem. Soc. Perkin Trans. 1*, pp. 1339–1344 (1986).

Herbert E. Carter et al. "Synthesis and Configuration of Dihydrosphingosine", *Journal of American Chemical Society*, vol. 75, pp. 1007–1008 (1953).

Tomas Hudlicky et al, "Biocatalysis as a Rational Approach to Enantiodivergent Synthesis of Highly Oxygenated Compounds: (+)– and (–)–Pinitol and Other Cyclotols", *Israel Journal of Chemistry*, vol. 31, pp. 229–238 (1991).

Hudlicky et al., "An Enantiodivergent Approach to D–and L–Erythrose Via Microbial Oxidation of Chlorobenzene, "*Tetrahedron Letters*, vol. 30, No. 31, pp. 4053–4054 (1989).

Schmidt and Zimmermann, "Synthesis of D-*Erythro*-Sphingosines,"*Tetrahedron Letters*, vol. 27, pp. 481–484 (1986).

Grob and Gadient, "Die Synthese des Sphingosins und seiner Stereoisomeren,"*Helvetica Chemica Acta*, vol. 40, pp. 1145–1157 (1957).

15, L-erythrose       16

FIGURE 4

SYNTHESIS OF SPHINGOSINES

This application is a continuation of application Ser. No. 08/137,346, filed Oct. 18, 1993 now abandoned.

BACKGROUND OF THE INVENTION

1. Field of the Invention

This invention relates to a method for the synthesis of sphingosines. More particularly, this invention relates to the synthesis of the four stereoisomers 1–4 of sphingosine by conversion of an achiral starting material.

2. Background of the Invention

Sphingosines constitute a group of related long-chain aliphatic 2-amino-1,3-diols, of which D-erythro-1,3-dihydroxy- 2-amino-4,5-trans-octadecene is the most frequently occurring in animal glycosphingolipids. Glycosphingolipids are the glycosides of N-acylsphingosine, the trivial name of which is ceramide. The structural variation in fatty acids, sphingosines, and carbohydrates results in a great number of chemically distinct glycosphingolipids. Thus, sphingosines and their derivatives, glycosphingolipids, are of interest because of their diverse bioactivities and biological roles. These activities include inhibition of protein kinase C activity and transfer of information between developing vertebrate cells. Sphingosines also serve as chain terminators in various gangliosides. Galactosyl ceramide has been shown to be a receptor for HIV binding in cells lacking the CD4 receptor.

In order to obtain valuable sphingosine derivatives, it is useful to first synthesize optically pure sphingosine in all its isomeric forms:

Previous methods of synthesizing optically pure sphingosines have relied on the use of serine as a chiral building block. For example, Newman, *J. Am. Chem.*, 95(12):4098 (1973); Boutin et al., *J. Org. Chem.*, 51:5320 (1986); Garner et al, *J. Org. Chem.*, 53:4395 (1988); Polt et al., *J. Org. Chem.*, 57:5469 (1992); Herold, *Helv. Chim. Acta*, 71:354 (1988); Nimkar et al., *Tetrahedron Letters*, 29(25):3037 (1988); and U.S. Pat. No. 5,110,987, describe the preparation of sphingosine or its derivatives from serine or related compounds. These methods are disadvantageous due to the impossibility of obtaining all four stereoisomers of sphingosine from the same starting compound. Moreover, methods utilizing serine as a starting material are quite lengthy and, thus, are not amenable to potential scale-up.

Another effort to synthesize optically pure sphingosines utilized the stereospecific hydration of chlorofumaric acid with fumarase to give L-threo-chloromalic acid as a chiral pool reagent and result in the synthesis of D-erythrosphingosine, as described in Findeis et al., *J. Org. Chem.*, 52:2838–2848 (1987). This method is complicated and only results in the synthesis of one stereoisomer of sphingosine.

Several attempts to obtain optically pure sphingosines have utilized carbohydrates as starting materials. In Zimmermann and Schmidt et al., *Liebigs Ann. Chem.*, 663 (1988), a method of synthesizing D-erythro-sphingosine is described utilizing D-galactose. U.S Pat. No. 4,937,328 describes the synthesis of sphingosine derivatives from D-galactose. Obayashi et al., *Chemistry Letters*, pp. 1715–1718 (1985), describes synthesis of sphingosines using sugar precursors. Using sugars as the starting material locks the design into a particular configuration of stereocenters. The necessary manipulations and inversions required to get a desired isomer then lengthen the synthesis process.

Despite the prior efforts, an efficient method for the synthesis of sphingosines has not heretofore been available. Further, there is a need in the art for a method for synthesizing sphingosines which enables the production of a desired stereoisomer.

Therefore, it is an object of the present invention to provide a general method for the synthesis of all sphingosines.

It is further an object of the present invention to provide a method for the synthesis of the four stereoisomers of sphingosine from the same starting material.

It is further an object of the present invention to provide a method for the synthesis of sphingosine using an easily obtainable starting material.

It is further an object of the present invention to provide a method for the synthesis of sphingosine which can yield the product in a minimum number of steps.

It is further an object of the present invention to provide an environmentally acceptable method for the synthesis of sphingosine.

These and other objects of the present invention will become apparent upon review of the following specification and the claims appended thereto.

SUMMARY OF THE INVENTION

In accordance with the foregoing objectives, there is provided by the present invention a process for the synthesis of a stereospecific sphingosine comprising providing an arene diol of the formula:

wherein X is H, halogen, OH, OR, phenyl, acetylene, $NH_2$, $N_3$, $NR_2$, NRH, $NO_2$, $CO_2H$, or CN and R is lower alkyl or lower alkenyl;

protecting the diol as its acetonide with the following formula:

converting the acetonide to an epoxide having the formula:

reacting the epoxide with an effective amount of an azide salt to stereospecifically open the epoxide and obtain an azido alcohol with the formula:

reacting the azido alcohol first with excess ozone and then with excess borohydride to give a first lactol with the formula:

reacting the first lactol with an acidic ion exchange resin to deprotect the first lactol and obtain a second lactol of the formula:

reacting the second lactol with an effective amount of an alkali periodate to obtain a third lactol with the formula:

subjecting the third lactol to Wittig olefination to give azidosphingosine, and reducing the azidosphingosine to an amine to obtain the desired sphingosine.

In another embodiment of the present invention, a stereospecific sphingosine is synthesized by a method including reacting the epoxide first with $FeCl_3$ and then with an azide salt to obtain a stereospecific azido alcohol.

In another embodiment of the present invention, a stereospecific sphingosine is synthesized by a method including reacting the epoxide first with LiCl in the presence of ethyl acetoacetate and then with an azide salt to obtain a stereospecific azido alcohol.

In another embodiment of the present invention, a stereospecific sphingosine is synthesized by a method including reacting the epoxide with an azide salt to obtain a stereospecific azido alcohol.

In a further embodiment of the present invention, there is provided a process for the synthesis of a stereospecific sphingosine from chlorobenzene via the intermediate 2,3-O-isopropylidene-L-erythrose.

With the foregoing and other objects, advantages and features of the invention that will become hereinafter apparent, the nature of the invention may be more clearly understood by reference to the following detailed description of the preferred embodiments of the invention, the figures and to the appended claims.

DETAILED DESCRIPTION OF THE PREFERRED EMBODIMENTS OF THE INVENTION

Biocatalytic conversion of chlorobenzene to the corresponding homochiral cyclohexadiene cis-diol has now been found to allow, through careful symmetry-based planning, the stereodivergent synthesis of sphingosine stereoisomers. In 1970, Gibson and co-workers reported the enantioselective oxidation of toluene to cis-toluenediol by a mutant of *Pseudomonas putida*, a soil bacterium. Gibson et al., *J. Biochemistry*, 9:1626 (1970). Since this time many other simple arenes were shown to yield diols of this type through microbial oxidation techniques.

The present invention takes advantage of the chirality introduced in the microbial oxidation of arene diols to effectively synthesize stereospecific sphingosines. Thus, surprisingly, a stereospecific sphingosine can be obtained from an achiral aromatic source. The sphingosines obtained in this manner are optically pure and can be used for the manufacture of useful glycosphingolipids or other derivatives. Moreover, synthesis of sphingosines by the process of the present invention enables economical scale-up of the process since all of the stereoisomers can be prepared using the same starting material and very similar synthesis reactants and procedures.

Figure 1:
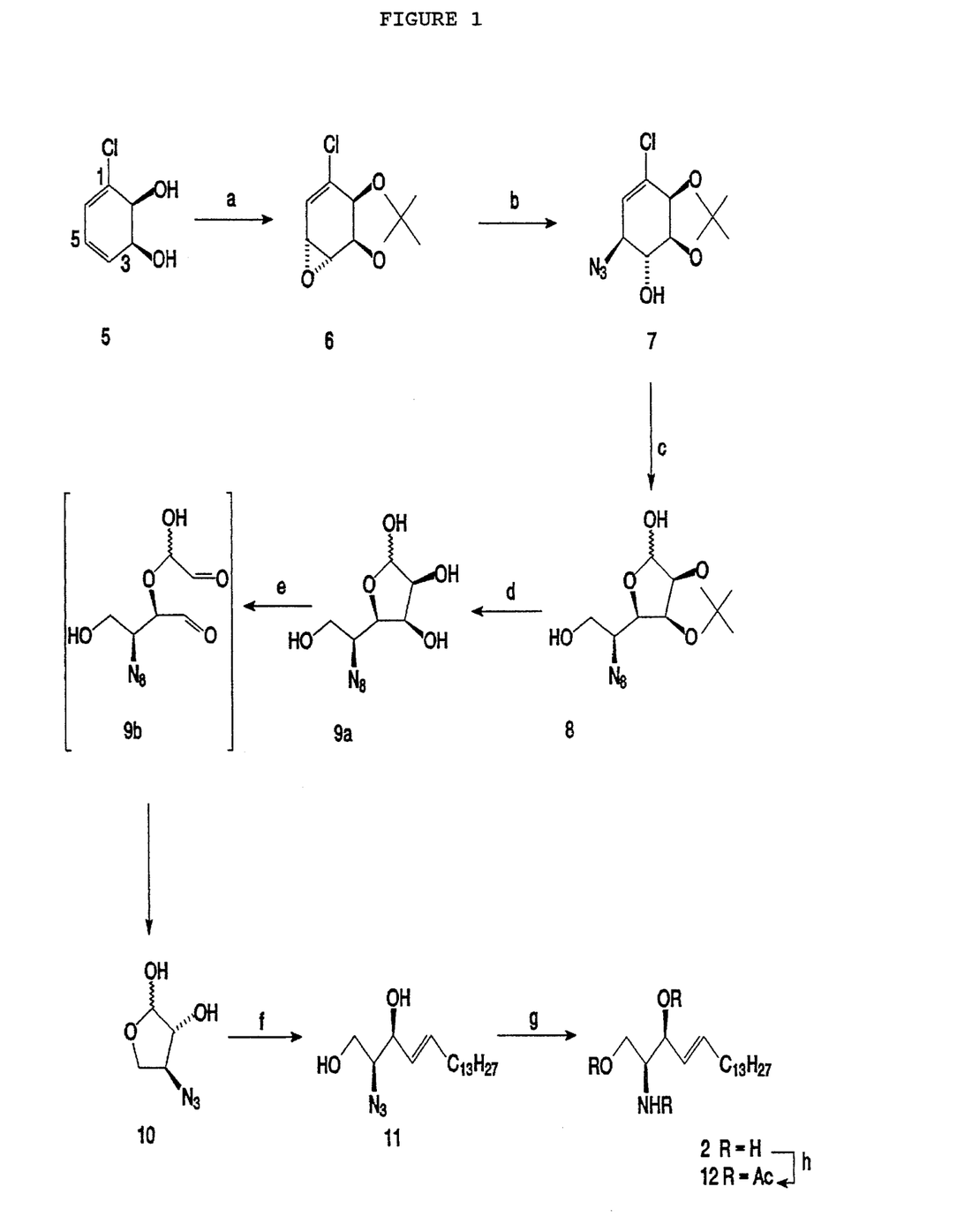
FIG. 1 illustrates the synthesis of L-threo-sphingosine or a derivative thereof according to the present invention. The letters a–h indicate the following reagents used: (a) (1) 2,2-dimethoxypropane, cat. p-TsOH, $CH_2Cl_2$, (2) mCPBA, $CH_2Cl_2$; (b) $NAN_3$, $NH_4$+Cl—, 1,2-dimethoxyethane/EtOH/$H_2O$, 70° C.; (c) (1) $O_3$, $CH_3OH$, −78° C., (2) $NaBH_4$, $CH_3OH$, 0° C. to RT; (d) Amberlyst acidic resin; (e) $NaIO_4$, $H_2O$; (f) n-tetradecyltriphenylphosphonium bromide 1.2eq, phenyllithium 4.4eq, toluene/THF, −30° C., quenched at 0° C.; (g) $H_2S$, pyridine; (h) acetic anhydride, pyridine.

FIG. 1 sets forth the synthesis of L-threo-sphingosine according to the present invention. This synthesis will be used throughout to illustrate the invention, but should not be construed as limiting the invention to the reactants and compounds shown therein.

The other isomers of sphingosine can be obtained by identical steps provided the other three isomers of azido alcohol are made. The azido alcohols which result in the sphingosine stereoisomers are as follows:

For the synthesis of sphingosine, a substituted benzenediol, preferably obtained by microbial oxidation with *Pseudomonas putida,* strain 39D, is first obtained. The diol may be obtained by microbial oxidation with other *Pseudomonas putida* strains, provided the proper diol is obtained. Benzenediols obtained via microbial oxidation may be commercially obtained from Genencor International, Rochester, N.Y., ICI Fine Chemicals, Manchester, U.K. or Enzymatics, Ltd., Cambridge, U.K.

In the preferred embodiment, the diol is chlorobenzenediol 5 ((2R, 3S)-2,3-dihydroxy-1-chlorocyclohexa 4,6-diene). However, almost any atom or functional group can be placed in the periphery of the aromatic ring with substitution limited only by the microbial process, i.e., by the substituted arenes which can serve as a substrate for the microbial process. Suitable substituents include H, halogen, OH, OR, phenyl, acetylene, $NH_2$, $N_3$, $NR_2$, NRH, $NO_2$, $CO_2H$, or CN and R is lower alkyl or lower alkenyl. Preferably, R has about one to six carbons. In a preferred embodiment, and as illustrated herein, X is Cl.

To obtain sphingosines 2 and 3, the benzenediol 5 is protected as its acetonide by reacting the diol with a ketone protecting reagent in the first step of a in FIG. 1. The diol is protected to allow selectivity in the subsequent reaction steps. In the rigid acetonides, only one face is open to the approach of an electrophilic reagent resulting in a stereocontrolled introduction of the next stereocenter.

Any ketone protecting reagent known to those of skill in the art may be used, such as acetone, 2,2-dimethoxypropane, cyclohexanone, among others. In a preferred embodiment, the diol is reacted with 2,2-dimethoxypropane in the presence of a catalyst, p-toluenesulfonic acid, and a solvent, methylene chloride. The reaction can take place in any suitable solvent, such as methylene chloride or acetone, among others. This reaction is described in U.S. Pat. No. 5,200,516, incorporated herein by reference.

For the synthesis of sphingosines 2 and 3, the acetonide is then converted to an anti epoxide 6, preferably by epoxidation of the acetonide with meta-chloroperbenzoic acid (mCPBA) in a suitable solvent in the second part of a in FIG. 1 (see U.S. Pat. No. 5,200,516). Preferably, the solvent is the same as that used in the reaction to obtain the acetonide, eliminating the need for multiple reaction vessels.

For the synthesis of sphingosines 1 and 4, the diol is directly reacted with mCPBA to obtain the Syn epoxide and protection as an acetonide as described above is conducted after the epoxidation step.

The anti epoxide 6 or the syn epoxide, depending on the desired isomer, is then reacted in step b with an effective amount of an azide salt to stereospecifically open the epoxide and obtain an azido alcohol 7, or azido alcohol isomer (see above). The preferred azide is sodium azide. Alternatively, other azide salts can be used including, but not limited to, lithium azide, potassium azide, cesium azide or a tetraalkylammonium azide. The reaction to obtain azido alcohol 7 is preferably carried out in the presence of ammonium chloride as a catalyst. 1,2-dimethoxyethane and ethanol are preferably used as the solvent, but other suitable solvents known to those of skill in the art may be used. In a preferred embodiment, the reaction is carried out at a temperature above room temperature, especially between about 55° and about 85° C. In the most preferred embodiment, the reaction is carried out at about 70° C.

The azide is provided in an amount effective to stereospecifically open the epoxide and form the desired azido alcohol. The azide will generally be used in slight excess to ensure complete reaction. This step allows the production of the desired sphingosine isomer. Discussions regarding the stereoselective generation of the azido alcohol may be found in Hudlicky et al., *J. Chem. Soc. Perkin Trans*, 1 pp. 2907–2917 (1991) and Hudlicky et al., *J. Org. Chem,*, 58:985 (1993), incorporated herein by reference.

The azido alcohol obtained will determine the stereoisomer of sphingosine to be obtained. The azido alcohol needed to synthesize D-erythro-sphingosine (1) may be obtained by reacting $FeCl_3$ with the syn epoxide and then reacting the product obtained therefrom with an azide salt.

The azido alcohol needed to synthesize L-threo-sphingosine (2) may be obtained by reacting the anti epoxide with an azide salt in the presence of ammonium chloride, as discussed above.

The azido alcohol needed to synthesize L-erythro-sphingosine (3) may be obtained by reacting the anti epoxide with LiCl in the presence of ethyl acetoacetate and then reacting the product therefrom with an azide salt.

The azido alcohol needed to synthesize D-threo-sphingosine (4) may be obtained by reacting the syn epoxide with an azide salt.

It is believed that any of the desired sphingosines can be produced by the same reaction sequence once the appropriate azido alcohol is provided. Therefore, the remaining steps discussed in the context of FIG. 1 will be substantially identical no matter which sphingosine is being synthesized.

In step c of FIG. 1, a two part reaction is conducted. First, the azido alcohol is reacted with excess ozone at low temperatures. A solvent, such as methanol may be used. The temperature of this reaction preferably will be about $-70°$ to about $-85°$ C., most preferably about $-78°$ C.

In the second part of the reaction designated c in FIG. 1, excess borohydride is reacted with the product from the ozonolysis to produce a first lactol 8. The preferred borohydride reagent is sodium borohydride. Other borohydride reagents could be used including, but not limited to, lithium, potassium or tetraalkylammonium borohydride. The temperature is preferably raised for this reaction to about $0°$ C. The reaction preferably is monitored by thin layer chromatography to ascertain when the reaction is complete. The reaction temperature may be raised to about room temperature, if required, to complete the reduction to the lactol 8.

The first lactol is then contacted in step d with an acidic ion exchange resin to deprotect it and form a second lactone 9a. Suitable ion acid exchange resins are commercially available from Aldrich or other companies. Some suitable resins include Amberlyst 15, Amberlyst IR 118, Amberlite CG-50, Dowex 50×8–100, among others.

The second lactol 9a is then reacted in step e with an effective amount of alkali metal periodate to produce a third lactol 10 by way of 9b. The alkali metal periodate can be, for example, the lithium, sodium or potassium salt. The preferred alkali metal periodate is sodium periodate.

The resulting lactol is then subjected to Wittig olefination in step f to produce azidosphingosine 11. The Wittig reaction generally is carried out in an inert gas atmosphere, for example under nitrogen, at low temperatures, using an aliphatic triphenylphosphonium halide in the presence of a base. For purposes of the production of sphingosine, n-tetradecyltriphenylphosphonium bromide is preferred. Suitable bases for the Wittig reaction include organic lithium compounds, such as phenyllithium, lithium methylate or lithium ethylate or compounds such as sodium amide, sodium methylate and sodium carbonate. In a preferred embodiment, the base is phenyllithium. Solvents which can be used are aromatic hydrocarbons, such as benzene, toluene or xylene, or ethers, such as diethyl ether, tetrahydrofuran or dioxane. In a preferred embodiment, the solvent is a toluene, THF, or a mixture thereof. Preferably, the solvent is anhydrous.

The Wittig reaction preferably takes place at temperatures of about $-25°$ to about $-40°$ C. In a preferred embodiment, the reaction takes place at about $-35°$ to about $-30°$ C.

The azidosphingosine is preferably reduced in step g to the desired sphingosine isomer. This reduction can be performed by any of the methods known in the art, such as by $H_2S$, $H_2$/catalyst(Pd), $LiAlH_4$ or $NaBH_4$, among others. In the preferred embodiment, the azidosphingosine is reduced with hydrogen sulfide in pyridine or other solvent.

If a derivative of the optically pure sphingosine prepared is desired, any of the known reactions available for obtaining such derivatives may be conducted. In FIG. 1, step h illustrates the acylation of sphingosine. To obtain compound 12, this step is carried out using acetic anhydride in a solvent, preferably, pyridine.

Figure 2:
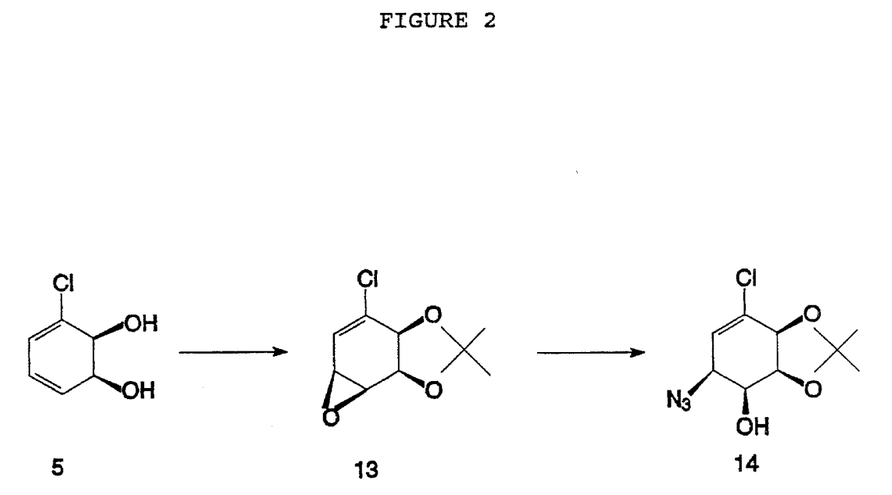
FIG. 2 illustrates the synthesis of the epoxide and azido alcohol which are used to synthesize D-erythrosphingosine.

FIG. 2 illustrates the intermediates obtained when synthesizing the sphingosine isomer D-erythro-sphingosine, which is the naturally found stereoisomer. Epoxide 13 is obtained by m-CPBA, as above, directed E by the diol and then protected by reaction with 2,2-dimethoxypropane or other ketone protecting reagent. The epoxide is then reacted first with $FeCl_3$ and then with an azide salt to obtain an azido alcohol 14. Treatment of azido alcohol 14 under the same reaction conditions deployed with azido alcohol 7 from FIG. 1 will lead to the natural isomer.

Figure 3:
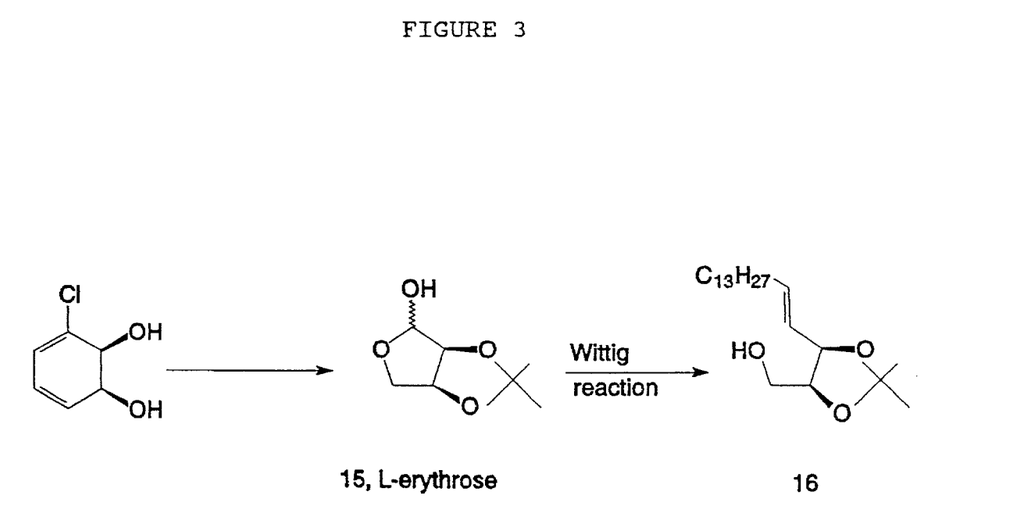
FIG. 3 illustrates the synthesis of an intermediate found to be useful for obtaining the stereoisomers of sphingosine according to the present invention, which intermediate is obtained from 2,3-O-isopropylidene L-erythrose synthesized from chlorobenzene.
Figure 4:
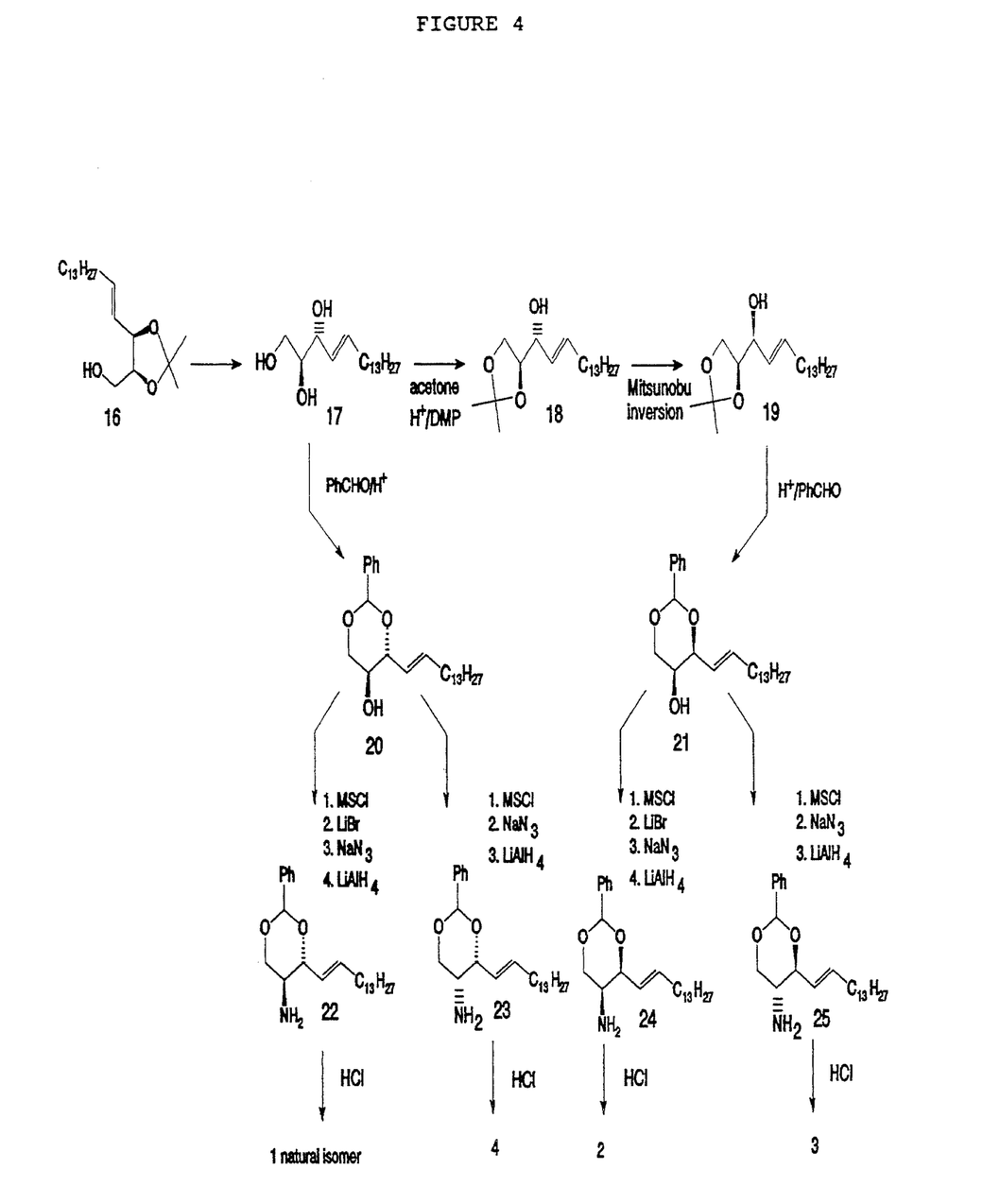
FIG. 4 illustrates the synthesis of the stereoisomers of sphingosine from the intermediate of FIG. 3.

In another embodiment of the present invention, the synthesis schemes of FIGS. 3 and 4 are employed. In particular, all four isomers can be obtained by use of the steps illustrated in FIGS. 3 and 4. These compounds are generated selectively for diastereo/enantiomeric distinction of the final products. Substitution with azide using single or double inversion will generate all stereoisomers.

As above, the starting material is a arene diol, preferably chlorobenzenediol. The diol is reacted to obtain 2,3-O-isopropyulidene-L-erythrose 15 as shown in Hudlicky et al., *J. Org. Chem.*, 55:4683 (1990), and U.S. Pat. No. 5,200,516, both incorporated herein by reference in their entireties. In general, the 2,3-O-isopropylidene-L-erythrose is synthesized as follows: treating (+)-cis-2,3-dihydroxy-1-chlorocyclohexa-4,6-diene with p-toluenesulfonic acid in the presence of 2,2-dimethoxypropane to form (2R,3S)-2,3-O-isopropylidene-1-chlorocyclohexa-4,6-diene; subjecting said (2R,3S)-2,3-O-isopropylidene-1-chlorocyclohexa- 4,6-diene to ozonolysis followed by cyclization of the product of said ozonolysis to form 2,3-O-isopropylidene-D-erythruronolactone; reducing said 2,3-O-isopropylidene-D-erythruronolactone in the presence of sodium borohydride to produce sodium (S,S)-2,3-O-isopropylidene-4-hydroxybutanoate; cyclizing said sodium (S,S)-2,3-O-isopropylidene- 4-hydroxybutanoate in the presence of iodomethane to form 2,3-O-isopropylidene-L-erythrono-1, 4-lactone; and treating said 2,3-O-isopropylidene-L-erythrono-1,4-lactone with DIBAL solution to form 2,3-O-isopropylidene-L-erythrose.

2,3-O-Isopropylidene-L-erythrose 15 is then subjected to the Wittig reaction using an aliphatic triphenylphosphonium halide in the presence of a base to obtain compound 16.

FIG. 4 illustrates the reaction paths for the synthesis of each sphingosine isomer from compound 16. To obtain isomers 1 and 4, compound 16 is first reacted with $H^+$ or acid to effect catalytic deprotection and provide compound 17. This compound is reacted with benzylaldehyde in the presence of acid to provide compound 20 which is reacted with methanesulfonyl chloride (MSCl), lithium bromide, sodium azide and lithium aluminum hydride in a four step reaction to provide compound 22 which is then subjected to hydrogen chloride to obtain sphingosine 1. Alternatively, compound 20 may be reacted with methanesulfonylchloride, sodium azide and lithium aluminum hydride in a three step reaction to provide compound 23 which is then subjected to hydrogen chloride to obtain sphingosine 4.

To obtain the other isomers, compound 17 is reacted with 2,2-dimethoxypropane in the presence of acid and acetone to obtain compound 18, which then undergoes Mitsunobu inversion (generally, diethyldiazo dicarboxylate, triphenylphosphene and benzoic acid as reactants, see U.S. Pat. No. 5,110,987, incorporated herein by reference) to compound 19. Compound 19 is reacted with benzaldehyde in the presence of acid to obtain compound 21 which then undergoes the same reactions as above to obtain compounds 24 and 25, which are reacted with hydrogen chloride to obtain sphingosines 2 and 3, respectively.

The procedures, reactants and reaction conditions for the above reactions will be readily understood by one of ordinary skill in the art.

The following examples illustrate the invention. It is understood, however, that these examples are not to be interpreted as limiting the scope of the invention.

EXAMPLES

Example 1—Production of L-threo-sphingosine

FIG. 1 illustrates the synthesis of L-threo-sphingosine and the numbered structures in FIG. 1 correspond to the numbered compounds whose synthesis is described herein.

Chlorobenzenediol 5 was obtained by enzymatic oxygenation of chlorobenzene with *Pseudomonas putida* 39D as taught in Hudlicky et al., *J. Am. Chem. Soc.,* 110(14):4735 (1988), incorporated herein by reference in its entirety. *P. putida* 39D was grown at 28° C. in MBS-arginine medium (75 mL) in a 250 mL Erlenmeyer flask. Toluene was supplied by a scale bulb attached to the flask by a neoprene stopper, and the culture was aerated on a reciprocal shaker. After 6 hours, the culture was centrifuged at 5000 rpm during 10 minutes, the medium was discarded, and the cells were suspended in 400 mL of fresh MBS-arginine medium and placed in a 1-L Erlenmeyer flask equipped with a bubbler. A stream of air/chlorobenzene (5:1 by volume) was bubbled through the medium controlled by a thermostat at 28°–29° C. After 24 hours the culture was centrifuged, the cells were discarded, and the pH of the medium was adjusted to 8.4 with aqueous NaOH. The solution was saturated with NaCl, centrifuged again, and extracted with ethyl acetate (acid-free, 5×100 mL). The organic extract was dried with $Na_2SO_4$, and solvent was evaporated and filtered through a small plug of silica gel (10% deactivated, hexane/ethyl acetate, 1:1) to give pure chlorobenzenediol as a white solid (0.40 g), mp 82°–84° C.

In a one-pot operation, the chlorobenzenediol 5 obtained was protected as an acetonide by the reaction of 2,2-dimethoxypropane in the presence of p-toluenesulfonic acid° To a solution of benzenediol (736.5 mg, 4.646 mmol), in 10 mL of 2,2-dimethoxypropane (DMP)-acetone (3:1) was added a catalytic amount of p-toluenesulfonic acid, and the reaction mixture was stirred at room temperature, protected from moisture, for 30 min. The dienediol was obtained as described by Gibson, et al. *Biochemistry* 9:1626 (1970). To the mixture was added 5 mL of 10% aqueous NaOH, and the reaction mixture was stirred for 10 min. The reaction mixture was diluted with 10 mL of ethyl acetate, and the organic layer was washed with brine (3×5 mL). The organic extracts were dried over sodium sulfate, and the solvent was evaporated, yielding 832 mg (95%) of a colorless liquid ((2S, 3S)-2,3-O-isopropylidene- 1-chlorocyclohexa-4,6-diene); $R_f$=0.8 (hexaneethyl acetate, 8:2); $[\alpha]^{25}_D$= +45$^\alpha$ (C 0.50, $CHCl_3$); IR (neat) 2988, 2935, 2898, 1652, 1380 cm$^{-1}$; $^1$H NMR ($CDCl_3$) δ 6.05 (d, J=5.5 Hz, 1H), 6.85 (m,2H), 4.7(dd, J=3.4 Hz, J=8.8 Hz, 1H) 4.57 (d, J=8.8 Hz, 1H), 1.36 (s, 6H); $^{13}$C NMR ($CDCl_3$) δ 133.3, 124.0, 123.2, 121.6, 106.3, 74.7, 72.6, 26.6, 24.9.

The resulting intermediate acetonide was subjected to epoxidation by reaction with m-CPBA in $CH_2Cl_2$ (75 mL). To a solution of the acetonide (1.915 g, 10.3 mmol) at 0° C. was added m-CPBA (1.78g, 8.2 mmol) portionwise. The solution was allowed to warm to room temperature and stirred for 8 hours. The reaction mixture was washed with 15% aqueous sodium sulfite (2×50 mL), saturated aqueous sodium bicarbonate (2×50 mL) and water (50 mL), then dried, filtered and concentrated. Unreacted starting material was removed under vacuum leaving 1.50 g (7.3 mmol, 89%) pure epoxide 6 as a colorless solid (1R, 4S, 5S, 6R)-3-chloro-4,5-di-O-isopropylidene-7-oxabicyclo[ 4.1.0]hept-2-ene); mp-59°–60° C.

The epoxide 6 was then subjected to stereospecific opening with sodium azide to yield an azido alcohol 7.

Epoxide (133 mg, 0.657 mmol), sodium azide (2.63 mmol, 171 mg), and dry ammonium chloride (2.63 mmol, 141 mg) were dissolved in a mixture of DME-EtOH-$H_2O$ (1.5:1:1), and the solution was heated at 80° C. for 1 h. After cooling, brine (15 mL) and ethyl acetate (5 mL) were added, with stirring continued for 10 min. The layers were separated, and the aqueous layer was extracted with ethyl acetate (3×5 mL). The combined organic extracts were dried ($Na_2SO_4$) and evaporated to produce 192 mg of a slightly yellow solid, which was purified by flash chromatography (silica gel, hexanes/ethyl acetate, 7:3) to produce pure azido alcohol 7 ((3S,4R,5S,6S)-3-azido-1-chloro-4-hydroxy-5,6-O-isopropylidene- 1-cyclohexene) in 88% yield (141 mg, 0.574 mmol). Analytical sample was obtained by recrystallization from $CH_2Cl_2$-hexane, $R_f$: 0.09 (silica gel; hexanes/ ethyl acetate, 8:2); Mp:94°–94.5° C. $[\alpha]_D^{23}$:–10.2° (C=0.96, MeOH). IR (film) 3454, 2113, 1250, 1085, 1074, 869 cm$^{-1}$. $^1$H NMR: ($CDCl_3$) δ 5.87 (d, J=2.1 Hz, 1H), 4.6 (d, J=6.4 Hz, 1H), 4.16 (dd, J=8.7, 6.4 Hz, 1H), 3.96 (dd, J=8.7, 1.4 Hz, 1H), 3.69 (td, J=8.6, 3.0 Hz, 1H), 2.88 (d, J=3.0 Hz, 1H), 1.53 (s, 3H), 1.40 (s, 3H). $_{13}$C NMR: ($CDCl_3$) δ 131.0 (C), 126.6 (CH), 111.5 (C), 77.9 (CH), 75.6, 73.1 (CH), 61.3 (CH), 28.1 (CH3), 25.9 (CH3). MS: (CI) m/z (rel. intensity) 246 (M+i) (40), 230 (100), 218 (20). Anal. calcd for $C_9H_{12}N_3O_3Cl$: C, 44.0; H, 4.92; N, 17.10. Found: C, 44.11; H, 4.92; N, 17.07.

The azido alcohol 7 (1097.0 mg, 4.465 mmoles) was placed in a reaction vessel (glass) with methanol (11 mL). This solution was cooled in a dry-ice/acetone bath and an excess of $O_3/O_2$ was bubbled through the solution for 25 minutes. Nitrogen was then bubbled through the solution for half an hour at –78° C. The reaction temperature was then raised to 0° C.

1.12 eq. of $NaBH_4$ (190 mg., 5.022 mmol) was then added over a 5 minute period. After half an hour this procedure was repeated. By thin layer chromatography (TLC) the reduction was not complete so the reaction temperature was raised to room temperature. After an additional 30 minutes, NaBH$_4$ (30 mg, 70 mg, 50 mg) was added every half hour in three portions (constant monitoring by TLC). The reaction was acidified using aqueous HCl (11.5 mL of 0.8 M) until pH=4.0. Extraction with EtOAc (4×), brine washing of the organic layer, MgSO$_4$ drying and removal of solvent yielded 1.260 g of crude product. Column chromatography yielded a clear oil 676.8 mg (2.760 mmol, 62%) of lactol 8 (see FIG. 1 for structure).

The properties of lactol 8 were determined as follows: R$_f$.38 (hexane, ethylacetate 1:1); IR (film) v 3400, 2105, 1650 cm$^{-1}$; $^1$H (CDCl$_3$) δ 5.42 (s, 1H), 4.76 (dd, J=5.9, 3.6 Hz, 1H), 4.64 (d, J=5.9 Hz, 1H), 4.27 (dd, J=12.2, 3.4 Hz, 1H), 4.14 (d, J=2.0 Hz, 1H), 3.85 (m, 2H), 3.74 (m, 1H), 2.95 (bs, 1H), 1.47 (s, 3H), 1.32 (s, 3H); $^{13}$C NMR (CDCl$_3$) δ 112.9(C), 100.9 (CH), 85.9(CH), 79.9 (CH), 79.5 (CH), 63.5 (CH), 62.1 (CH$_2$), 25.9 (CH$_3$), 24.8 (CH$_3$); MS (CI, 70 eV) m/z (tel. intensity) 246 (M$^{+1}$, 4), 230 (85), 218 (90), 202 (100), 188(100), 170(100), 160(100).

Water (2 mL) was added to the lactol 8 (49.4 mg, 0.2014 mmol), followed by Amberlyst 15 (wet) ion-exchange resin (261 mg). The temperature was raised to 65° C.; after 5 hours, the reaction was finished by TLC. The solution was filtered and the pH adjusted to 7.0 with saturated NaHCO$_3$. This solution was diluted with H$_2$O until the total volume was 5 mL. NaIO$_4$ (51.7 mg, 0.2417 mmol) was added. After 8 hours, the reaction was finished by TLC. The product was extracted with EtOAc/EtOH (1:1); the organic layer was dried with MgSO$_4$ and the solvent removed. Column Chromatography (hexane/EtOAc 1:4) yielded 18.8 mg (0.1295 mmol, 64%) of a clear oil having the structure of lactol 10, shown in FIG. 1.

Lactol 10 was found to have the following properties: R$_f$=.36 (hexane/EtOAc, 1:4); IR (film) v 3400, 2105, 1660, 1640 cm$^{-1}$; $^1$H NMR (DMSO) δ 6.38 (m, 2H), 5.60 (d, J=4.4 Hz, 1H), 5.30 (d, J=6.8 Hz, 1H) 5.06 (t, J=5.4, 4.5 Hz, 1H), 5.00 (dd, J=4.6, 1.3 Hz, 1H), 4.02 (m, 3H), 3.80 (m, 2H), 3.70 (m, 1H), 3.40 (m, 2H); $^{13}$C NMR (DMSO) δ 102.5 (CH), 95.7 (CH'), 80.4 (CH), 75.8 (CH,), 65.3 (CH), 64.7 (CH,), 68.3 (CH$_2$), 66.7 (CH$_2$'); MS (CI 70 eV) m/z (rel. intensity) 128 (15), 118(8), 103(6), 88 (93), 73 (30), 60 (100).

To a round bottom flask was added n-tetradecyltriphenylphosphonium bromide (371. 159 mg, 0.688 mmol) followed by toluene (6.0 mL); the temperature was then lowered with an ice-bath. Phenyllithium (1.53 mL of a 1.8 M solution) was subsequently added over a ten minute period (the solution initially colorless turned a dark reddish brown). This was stirred for 15 minutes and then the temperature was lowered to 40° C. The bath temperature was then maintained between −35° C. and −30° C. for 40 minutes of which the first 20 minutes were used to add the lactol 10 (86.8 mg, 0.598 mmol, dissolved in THF (2.0 mL)). The temperature was then raised to 0° C. over 30 minutes and the reaction quenched with CH$_3$OH (2.0 mL) and then H$_2$O (2.0 Ml). Extraction with EtOAc, MgSO$_4$, drying, and column chromatography yielded 5.3 mg (2.72%) of a 2:1 (trans/cis) mixture of olefins, having the structure 11 shown in FIG. 1.

The properties of azidosphingosine 11 were as follows: $^1$H NMR (CDCl$_3$) δ 5.80 (m, 1H), 5.54 (m, 1H), 4.24 (t, 1H), 3.91 (m, 1H), 3.75 (m, 1H), 3.43 (m, 1H), 2.1 (m, 8H), 1.25 (m, 50H), 0.85 (t, 7H). Assignment was aided by $^1$H NMR of pure cis-azidosphingosine.

The azidosphingosine was then reacted with hydrogen sulfide in pyridine (see Schmidt, *Liebigs. Ann. Chem.*, 663–667 (1988) and U.S. Pat. No. 4,937,328, incorporated herein by reference) to yield L-threo-sphingosine.

L-threo-sphingosine (2)

Example 2—Production of (3R,4R, SS,6S)-3-azido-1-chloro-5,6-O-isopropylidene-4-hydroxy-1-cyclohexene To a solution of epoxide as prepared in example 1 (615mg, 3.04 mmol) in anhydrous THF (30 ml) were added ethyl acetoacetate (1.16 mL, 9.1 mmol) and lithium chloride (643 mg, 1.51 mmol) at room temperature. After stirring for 16 hours at 45° C., the reaction was quenched with saturated NH$_4$Cl (10 mL) and brine (10 mL). After separation, the aqueous layer was extracted with CH$_2$Cl$_2$ (2×20 mL). The organic extracts were washed with brine (1×15 mL), dried with Na$_2$SO$_4$ and the solvent evaporated. The crude product was purified by flash chromatography (silica gel, hexane/ ethyl acetate, 3:1) producing the corresponding trans-chlorohydrin in 91% yield (664 mg, 2.78 mmol) and traces of the cis-chlorohydrin (2-3%). trans-chlorohydrin; R$_f$: 0.38 (hexane/ethyl acetate, 3:1) . [α$_D^{26}$]: −7.3° (C=2.08, CHCl$_3$). IR: (neat) 3436, 2990, 1649, 1081 cm$^{-1}$. $^1$H $^1$NMR: (CDCl$_3$) δ 6.04 (dd, J=2.0, 1.0 Hz, 1H), 4.63 (d, J=6.3 Hz, 1H), 4.38 (ddd, J=8.4, 2.0, 1.0 Hz, 1H), 4.18 (dd, J=8.4, 8.4 Hz, 1H), 3.81 (t, J=8.4 Hz, 1H), 3.11 (br s, 1H), 1.56 (s, 3H), 1.43 (s, 3H). $^{13}$C MMR; (CDCl$_3$) δ 130.5 (C), 128.7 (C), 111.6 (C), 77.5 (CH), 75.7 (CH) 74.3 (CH), 58.2 (CH), 28.0 (CH3), 25.9 (CH3). M$_8$. (CI) m/z (rel. intensity) 239 (M+I, 100), 223 (20), 145 (20), 89 (18). calcd for C$_9$H$_{13}$Cl$_2$O$_3$: 239. 024175. Found: 239. 021317.

To a solution of the trans-chlorohydrin (664 mg, 2.78 mmol) in dry DMF (30 mL) sodium azide (542 rag, 8.33 mmol) was added under argon atmosphere. The reaction mixture was stirred at room temperature for 24 hours, and then at 55° C. for 12 hours. The reaction mixture was diluted with ether (30 mL) and washed with 10% Na$_2$S$_2$O$_3$ (20 mL). After separation, the aqueous layer was extracted with Et$_2$O (2×20 mL). The combined organic layer was washed with brine, dried (Na$_2$S$_2$O$_4$), and the solvent evaporated. The resulting oil was purified by flash chromatography (silica gel; hexane/ethyl acetate, 3: 1) producing the azido alcohol precursor to sphingosine 3 in 91% yield (621 mg, 2.53 mmol) and 2.7% (18 mg, 0.075 mmol) of the starting trans-chlorohydrin. R$_f$: 0.5 (hexane/ethyl acetate, 3:1). Mp: 93.5°–94° C. (CH$_2$Cl$_2$/hexane) . [α]$_D^{27}$: −99° (c=0.68, MeOH). IR: (KBr) 3884, 2115, 1651, 1383 cm$^{-1}$. $^1$H NMR: (CDCl$_3$) δ 5.9 (dd, J=3.6, 0.5 Hz, 1H), 4.58 (dd, J=5.6, 1.1 Hz, 1H), 4.39 (t, J=5.6 Hz, 1H), 4.23 (m, 1H), 4.19 (m, 1H), 2.49 (br s, 1H), 1.42 (s, 3H), 1.38 (s, 3H). $^{13}$C NMR: (CDCl$_3$) δ 134.7 (C), 122.2 (CH), 110.9 (C), 75.9 (CH), 75.0 (CH), 69.4 (CH), 27.6 (CH3), 26.0 (CH3). MS: (CI) m/z (rel. intensity) 246 (M+, 100), 160 (35), 145 (60), 96 (100). Amal. calc for C9H$_{12}$ClN$_{12}$O$_3$: C, 44.00; H, 4.92; N, 17.10. Found: C, 44.05; H, 4.95; N, 17.03.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A process for the synthesis of a stereospecific sphingosine comprising a. providing an arene diol of the formula:

wherein X is H, halogen, OH, OR, phenyl, acetylene, $NH_2$, $N_3$, $NR_2$, NRH, $NO_2$, $CO_2H$, or CN and R is lower alkyl or lower alkenyl;

b. protecting the diol as its acetonide with the following formula:

c. converting the acetonide to an epoxide having the formula:

d. reacting the epoxide with an effective amount of an azide salt to stereospecifically open the epoxide and obtain an azido alcohol with the formula:

e. reacting the azido alcohol with excess ozone and then with excess borohydride to give a first lactol with the formula:

f. reacting the first lactol with an acidic ion exchange resin to deprotect the first lactol and obtain a second lactol of the formula:

g. reacting the second lactol with an effective amount of an alkali periodate to obtain a third lactol with the formula:

h. subjecting the third lactol to Wittig olefination to give azidosphingosine; and i. reducing the azidosphingosine to an amine to obtain the desired sphingosine.

2. The process of claim 1, wherein the diol is obtained from microbial oxidation of Pseudomonas putida, strain 39D.

3. The process of claim 1, wherein the diol is protected as its acetonide by reacting the diol with 2,2-dimethoxypropane.

4. The process of claim 1, wherein the acetonide is converted to the epoxide by reacting the acetonide with m-chloroperbenzoic acid.

5. The process of claim 1, wherein the alkali metal azide is sodium azide.

6. The process of claim 1, wherein the borohydride is sodium borohydride.

7. The process of claim 1, wherein the alkali metal periodate is sodium periodate.

8. The process of claim 1, wherein the reduction of the azidosphingosine is carried out with hydrogen sulfide.

9. The process of claim 1, further comprising acylating the sphingosine with acetic anhydride.

10. The process of claim 1, wherein X is Cl.

11. A process for the synthesis of L-threo-sphingosine comprising:

a. protecting chlorobenzenediol by reacting the diol with 2,2-dimethoxypropane to obtain an intermediate acetonide;

b. converting the acetonide to an epoxide by reaction with m-chloroperbenzoic acid in methylene chloride;

c. reacting the epoxide with an effective amount of sodium azide in ammonium chloride to stereospecifically open the epoxide and obtain an azido alcohol;

d. reacting the azido alcohol first with excess ozone and then with excess borohydride to obtain a first lactol;

e. reacting the first lactol with an acidic ion exchange resin to deprotect the first lactol and obtain a second lactol;

f. reacting the second lactol with an effective amount of sodium periodate to obtain a third lactol;

g. subjecting the third lactol to Wittig olefination with n-tetradecyltriphenylphosphonium bromide to give azidosphingosine; and h. reducing the azidosphingosine to an amine to obtain L-threo-sphingosine.

12. A process for the synthesis of D-erythro-sphingosine comprising:
   a. converting chlorobenzenediol to an epoxide by reaction with m-chloroperbenzoic acid in methylene chloride;
   b. protecting the epoxide by reacting the epoxide with 2,2-dimethoxypropane to obtain a protected epoxide;
   c. reacting the protected epoxide first with FeCl$_3$ and then with an effective amount of sodium azide to stereospecifically open the epoxide and obtain an azido alcohol;
   d. reacting the azido alcohol first with excess ozone and then with excess borohydride to obtain a first lactol;
   e. reacting the first lactol with an acidic ion exchange resin to deprotect the first lactol and obtain a second lactol;
   f. reacting the second lactol with an effective amount of sodium periodate to obtain a third lactol;
   g. subjecting the third lactol to Wittig olefination with n-tetradecyltriphenylphosphonium bromide to give azidosphingosine; and
   h. reducing the azidosphingosine to an amine to obtain D-erythro-sphingosine.

13. A process for the synthesis of L-erythro-sphingosine comprising:
   a. protecting chlorobenzenediol by reacting the diol with 2,2-dimethoxypropane to obtain an intermediate acetonide;
   b. converting the acetonide to an epoxide by reaction with m-CPBA in methylene chloride;
   c. reacting the epoxide first with an effective amount of lithium chloride in the presence of ethyl acetoacetate and then with an effective amount of sodium azide to stereospecifically open the epoxide and obtain an azido alcohol;
   d. reacting the azido alcohol first with excess ozone and then with excess borohydride to obtain a first lactol;
   e. reacting the first lactol with an acidic ion exchange resin to deprotect the first lactol and obtain a second lactol;
   f. reacting the second lactol with an effective amount of sodium periodate to obtain a third lactol;
   g. subjecting the third lactol to Wittig olefination with n-tetradecyltriphenylphosphonium bromide to give azidosphingosine; and
   h. reducing the azidosphingosine to an amine to obtain L-erythro-sphingosine.

14. A process for the synthesis of D-threo-sphingosine comprising:
   a. converting chlorobenzenediol to an epoxide by reaction with m-chloroperbenzoic acid in methylene chloride;
   b. protecting the epoxide by reacting the epoxide with 2,2-dimethoxypropane to obtain a protected epoxide;
   c. reacting the epoxide with an effective amount of sodium azide to stereospecifically open the epoxide and obtain an azido alcohol;
   d. reacting the azido alcohol first with excess ozone and then with excess borohydride to obtain a first lactol;
   e. reacting the first lactol with an acidic ion exchange resin to deprotect the first lactol and obtain a second lactol;
   f. reacting the second lactol with an effective amount of sodium periodate to obtain a third lactol;
   g. subjecting the third lactol to Wittig olefination with n-tetradecyltriphenylphosphonium bromide to give azidosphingosine; and
   h. reducing the azidosphingosine to an amine to obtain D-threo-sphingosine.

* * * * *